United States Patent [19]

Scopes et al.

[11] Patent Number: 4,923,863
[45] Date of Patent: May 8, 1990

[54] MORPHOLINE DERIVATIVES, PHARMACEUTICAL COMPOSITIONS AND USE

[75] Inventors: David I. C. Scopes, Furneux Pelham; David E. Bays, Ware, both of United Kingdom

[73] Assignee: Glaxo Group Limited, London, England

[21] Appl. No.: 362,170

[22] Filed: Jun. 6, 1989

[30] Foreign Application Priority Data

Jun. 9, 1988 [GB] United Kingdom ............... 8813714

[51] Int. Cl.$^5$ ............... A61K 31/535; C07D 265/30; C07D 413/06
[52] U.S. Cl. ............... 514/235.5; 514/236.8; 514/237.5; 544/131; 544/137; 544/141; 544/162; 544/167
[58] Field of Search ............... 544/131, 137, 141, 162, 544/167; 514/235.5, 236.8, 237.5

[56] References Cited

U.S. PATENT DOCUMENTS 2,428,239  9/1947  Parker et al. ............... 544/162
3,586,713  6/1971  Buu-Hoi et al. ............... 544/162

Primary Examiner—Robert W. Ramsuer
Attorney, Agent, or Firm—Bacon & Thomas

[57] ABSTRACT

Compounds are disclosed of formula (I):

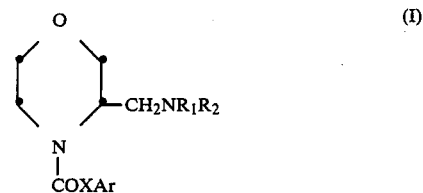

wherein
$R_1$ and $R_2$ are the same or different and are $C_{1-6}$ alkyl or $C_{3-6}$ alkenyl; or —$NR_1R_2$ forms a 5-membered (optionally containing an oxygen atom adjacent to the nitrogen) or a 6-membered ring, which ring optionally contains one unit of unsaturation and which is unsubstituted or substituted by hydroxy, oxo, optionally substituted methylidene, —$COR_3$ (where $R_6$ represents $C_{1-6}$ alkyl, $OR_4$ or —$NHR_4$, and $R_4$ represents hydrogen, $C_{1-6}$ alkyl, aryl, ar($C_{1-6}$)alkyl) or =$NOR_5$ (where $R_5$ represents $C_{1-6}$ alkyl);
X represents a direct bond, —$CH_2$— or —$CH_2O$—;
Ar represents a substituted phenyl moiety;
and physiologically acceptable salts thereof.

The compounds are indicated as useful for the treatment of pain and cerebral ischaemia.

Processes and intermediates for their preparation and pharmaceutical compositions containing them are also disclosed.

7 Claims, No Drawings

MORPHOLINE DERIVATIVES, PHARMACEUTICAL COMPOSITIONS AND USE

This invention relates to morpholine derivatives, to processes for their preparation, to pharmaceutical compositions containing them and to their medical use. In particular, the invention relates to compounds which act as agonists at kappa opioid receptors.

Compounds which are kappa opioid receptor agonists have been indicated in the art for the treatment of a number of conditions and have been described, for example, as analgesics, as diuretics and in the treatment of cerebral ischaemia. Opioid analgesia is generally thought to be mediated by either mu or kappa receptors in the brain (see, for example, Tyers M. B., *Br. J. Pharmacol*, (1980), 69, 503–512). Most existing clinically used opioid analgesics such as morphine and codeine act as mu-receptor agonists. However, these compounds have undesirable and potentially dangerous dependence forming side effects. There is thus a need for a strong analgesic with low dependence liability and a compound which is a selective kappa-receptor agonist would fulfil such a role.

Cerebral ischaemia or lack of blood flow in the brain, may result from a number of conditions, including, for example, stroke, head injuries or brain tumour. The resulting lack of oxygen to the brain cells causes neuronal damage and depending on the region of the brain involved, death or permanent disability may occur.

We have now found a novel group of morpholine derivatives which are selective kappa opioid receptor agonists. These compounds are therefore of interest in the treatment of conditions where the underlying aetiology indicates that treatment with a kappa opioid receptor agonist would be beneficial.

Thus, the present invention provides compounds of formula (I):

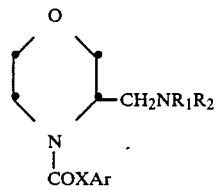

wherein $R_1$ and $R_2$ are the same or different and are $C_{1-6}$ alkyl or $C_{3-6}$ alkenyl; or $-NR_1R_2$ forms a 5-membered (optionally containing an oxygen atom adjacent to the nitrogen) or a 6-membered ring, which ring optionally contains one unit of unsaturation and which is unsubstituted or substituted by hydroxy, oxo, optionally substituted methylidene, $-COR_3$ (where $R_6$ represents $C_{1-6}$ alkyl, $OR_4$ or $-NHR_4$, and $R_4$ represents hydrogen, $C_{1-6}$ alkyl, aryl, ar($C_{1-6}$)alkyl) or $=NOR_5$ (where $R_5$ represents $C_{1-6}$ alkyl);

X represents a direct bond, $-CH_2-$ or $-CH_2O-$;
Ar represents a substituted phenyl moiety;
and physiologically acceptable salts thereof.

As used herein, a $C_{1-6}$ alkyl group or the alkyl moiety of an ar($C_{1-6}$)alkyl group may be straight or branched chain and is conveniently $C_{1-4}$ alkyl for example methyl or ethyl. An aryl group or the aryl moiety of an ar($C_{1-6}$)alkyl group is conveniently phenyl. An alkenyl group may be a straight or branched chain group containing one or more units of unsaturation which may be conjugated or unconjugated. Where $R_1$ and/or $R_2$ in the compounds of formula (I) represents an alkenyl group, it will be appreciated that a double bond will not be attached to the carbon atom adjacent to the nitrogen.

The term 'optionally substituted methylidene' as used herein includes methylidene substituted by any substituent conventional in the art. In the compounds of formula (I), the methylidene group may conveniently be substituted to form a conjugated system. Suitable substituents which form a conjugated system with the methylidene double bond include, for example, nitrile, phenyl, carboxyl and amido. Alternatively the methylidene group may conveniently be substituted by, for example, by a $C_{1-6}$ alkyl group, an ar($C_{1-6}$)alkyl group such as phenethyl, a $C_{1-6}$ hydroxyalkyl group such as hydroxymethyl, a $C_{1-6}$ carboxyalkyl group such as methoxycarbonylethyl or a $C_{1-6}$ amidoalkyl group such as aminocarbonylethyl.

Where $-NR_1R_2$ forms a substituted or unsubstituted 5 or 6-membered ring optionally containing one unit of unsaturation this may be, for example, a substituted or unsubstituted pyrrolidine, isoxazolidine or tetrahydropyridine ring. It will be appreciated that where the ring formed by $-NR_1R_2$ contains a unit of unsaturation, this will not be attached to a carbon atom adjacent to the nitrogen atom.

The term 'a substituted phenyl moiety' as used herein includes a phenyl moiety substituted by one or more conventional substituents in the art, which substituents may form a second ring optionally containing one or more units of unsaturation. In the compounds of formula (I), Ar conveniently represents a phenyl moiety which is substituted by one or more $C_{1-6}$ alkyl groups or electron-withdrawing substituents, or in which two adjacent substituents form a second ring. Suitable electron-withdrawing substituents include, for example, halogen (for example, fluorine, chlorine or bromine), $-CF_3$ or $-NO_2$. Where two substituents on the phenyl ring form a second ring, Ar may suitably represent naphthyl, for example 1-naphthyl or 2-naphthyl. Ar is preferably substituted at the meta and/or para positions on the phenyl ring by one or more halogens, for example chlorine and is typically a 3,4-dichlorophenyl moiety.

$R_1$ and $R_2$ may each independently represent a $C_{1-6}$ alkyl group such as methyl, or $-NR_1R_2$ may suitably represent a pyrrolidine or tetrahydropyridine ring which may be optionally substituted, for example, by $-CO_2CH_3$, preferably by $-OH$, $=CH_2$, $=NOCH_3$, $-CONH_2$ or more preferably by $=O$, $=CHCN$ or $=CHCO_2CH_3$.

$-NR_1R_2$ conveniently represents a substituted tetrahydropyridine or pyrrolidine ring but $-NR_1R_2$ preferably represents an unsubstituted tetrahydropyridine or more preferably an unsubstituted pyrrolidine ring. Where $-NR_1R_2$ represents a substituted ring, the substituent is preferably attached to the carbon atom β to the nitrogen atom.

X preferably represents $-CH_2-$.

A preferred class of compounds falling within the scope of formula (I) is that in which $-NR_1R_2$ forms a substituted or more preferably an unsubstituted pyrrolidine or tetrahydropyridine ring; X represents $-CH_2-$; Ar represents halosubstituted phenyl; and physiologically acceptable salts thereof. Particularly preferred compounds falling within this class are those in which Ar represents chlorosubstituted phenyl.

A preferred compound of the invention is 4-[(3,4-Dichlorophenyl)acetyl]-3-(1-pyrrolidinylmethyl)morpholine and its physiologically acceptable salts.

Compounds of formula (I) contain at least one chiral centre and may exist in more than one stereoisomeric form. The invention includes within its scope all enantiomers, diastereomers and mixtures thereof. The invention also embraces all geometric isomers of compounds of formula (I).

Suitable physiologically acceptable salts are those conventionally known in the art. Examples of physiologically acceptable salts include acid addition salts formed with inorganic acids, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention.

Compounds of the invention may readily be isolated in association with solvent molecules by crystallisation from or evaporation of an appropriate solvent. It is intended to include such solvents within the scope of the present invention.

Compounds falling within formula (I) have been shown to have analgesic activity using standard laboratory animal tests such as the mouse abdominal constriction test (M. B. Tyers, *Brit. J. Pharmacol*, 1980, 69, 503–512) or the rat paw pressure test. Furthermore, their kappa receptor activity has been demonstrated in vitro in the field stimulated rabbit vas deferens preparation using the procedure described in A. G. Hayes and A. Kelly, *Eur. J. Pharmacol* 110, 317–322 (1985). Compounds of the invention and their physiologically acceptable salts thus possess analgesic activity with the potential for low dependence liability and are therefore useful in the relief of pain.

Compounds of the invention are also of value in protecting against neuronal damage resulting from cerebral ischaemia which may be demonstrated for example in standard laboratory bilateral carotid occlusion models. Thus, compounds of the invention and their physiologically acceptable salts are also useful in treating or relieving the effects of cerebral ischaemia.

Accordingly, the invention also provides a compound of formula (I) or a physiologically acceptable salt thereof for use in medicine, in particular for the treatment of conditions where kappa agonists are indicated, (for example as analgesics and in the treatment of cerebral ischaemia).

In an alternative or further aspect there is provided a method of treatment of a mammal, including man, comprising administration of an effective amount of a compound of formula (I) or a physiologically acceptable salt thereof in particular in the treatment of conditions where the use of a kappa receptor agonist is indicated.

The invention also provides the use of a compound of formula (I) or a physiologically acceptable salt thereof for the manufacture of a medicament for the treatment of conditions where kappa receptor agonists are indicated.

It will be appreciated that compounds of the invention will primarily be of use in the alleviation of established symptoms but prophylaxis is not excluded.

Compounds of the invention may be administered as the raw chemical but the active ingredient is preferably presented as a pharmaceutical formulation. The active ingredient may conveniently be presented in unit dose form.

It will be appreciated that compounds of the invention will primarily be of use in the alleviation of established symptoms but prophylaxis is not excluded.

Compounds of formula (I) may be administered as the raw chemical but the active ingredient is preferably presented as a pharmaceutical formulation. The active ingredient may conveniently be presented in unit dose form.

Thus, according to another aspect, the invention provides a pharmaceutical composition comprising at least one compound of formula (I) or a physiologically acceptable salt thereof and formulated for administration by any convenient route conventional in the art. Such compositions are preferably in a form adapted for use in medicine, in particular human medicine and can conveniently be formulated in conventional manner and normally using one or more pharmaceutically acceptable carriers or excipients. Compounds according to the invention may conveniently be formulated for oral or parenteral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds of the invention may be formulated for parenteral administration by injection conveniently intravenous or subcutaneous injection, for example by bolus injection or continuous intravenous infusion. Where the compounds are administered by continuous intravenous infusion this is conveniently sequential to a bolus injection. Formulations for injection may be presented in unit dosage form, for example, in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed dose of the compounds of the invention for the relief of pain or the treatment of cerebral ischaemia is 0.01 to 100 mg/kg body weight, preferably 0.01 to 10 mg/kg body weight, most preferably 0.1 to 10 mg/kg body weight per day.

According to another aspect of the invention, compounds of formula (I) may be prepared by the general methods outlined below. In the following methods, $R_1$, $R_2$, X and Ar are as defined for formula (I) unless otherwise indicated.

It will be appreciated that in the methods for preparing compounds of formula (I) given below, it may be necessary or desirable to protect one or more sensitive groups in the molecule to prevent undesirable side reactions. Thus, a reaction step involving deprotection of a protected derivative of a compound of the invention may be required subsequent to any of the processes described below. Protection and deprotection may be effected using conventional procedures as described, for example, in 'Protective Groups in Organic Synthesis', T. W. Greene (John Wiley & Sons, 1981).

According to one general process (A), compounds of formula (I) may be prepared by reacting a compound of formula (II)

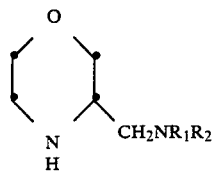 (II)

with a reagent serving to introduce the group —COXAr.

Thus, for example, compounds of formula (I) may be prepared by reacting a compound of formula (II) with an acid $ArXCO_2H$ or an acylating agent corresponding thereto or a salt thereof.

Suitable acylating agents corresponding to the acid $ArXCO_2H$ which may conveniently be used include, for example, acid halides (for example acid chlorides), alkyl esters (for example, methyl or ethyl esters) and mixed anhydrides. Such acylating agents may conveniently be prepared from the acid itself by conventional methods.

The reaction of a compound of formula (II) with an acid $ArXCO_2H$ is desirably effected in the presence of a coupling agent such as carbonyldiimidazole, dicyclohexylcarbodiimide or diphenylphosphoryl azide in a suitable reaction medium and conveniently at a temperature of from $-50°$ to $+50°$ C., preferably at ambient temperature. The reaction may be effected in a suitable reaction medium such as an ether (for example tetrahydrofuran), a haloalkane (for example, dichloromethane), a nitrile (for example acetonitrile), an amide (for example dimethylformamide), or mixtures thereof.

The reaction of a compound of formula (II) with an acylating agent corresponding to the acid $ArXCO_2H$ may conveniently be effected in a reaction medium and at a temperature as described above and optionally in the presence of a base. Suitable bases which may be employed include, for example, organic bases such as pyridine or triethylamine or inorganic bases such as calcium carbonate or sodium bicarbonate.

Compounds of formula (II) may conveniently be prepared from readily obtained starting materials by methods known in the art. For example compounds of formula (II) may be prepared from compounds of formula (III)

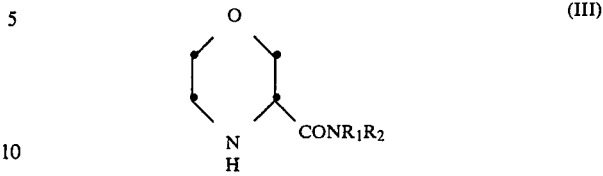 (III)

by reduction using a suitable reducing agent, for example a metal hydride such as lithium aluminium hydride in a solvent such as tetrahydrofuran.

Compounds of formula (III) may themselves be prepared, for example, from the appropriate carboxylic acid (IV)

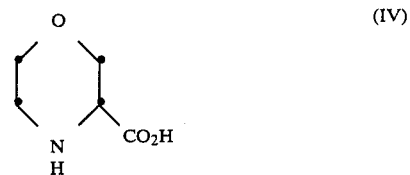 (IV)

or an acylating derivative corresponding thereto by reaction with an amine $R_1R_2NH$ according to the method described above. The starting carboxylic acid is a known compound (see, for example, Asher et. al., Tetrahedron Lett, 1981, 22, 141).

According to another general process (B), compounds of formula (I) may be prepared by reductive amination of a compound of formula (V).

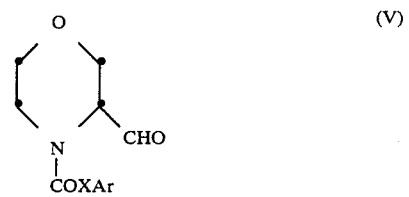 (V)

with an amine $R_1R_2NH$ in the presence of a suitable reducing agent.

The reduction may be effected using an alkali or alkaline earth metal borohydride or cyanoborohydride (for example sodium borohydride or cyanoborohydride) in a suitable solvent, for example an alcohol such as methanol and at a suitable temperature, conveniently room temperature. The reaction may optionally be performed in the presence of an acid such as acetic acid.

Alternatively, the reduction may be effected catalytically, for example, using hydrogen in the presence of a metal catalyst such as Raney nickel, platinum, platinum oxide, palladium or rhodium which may be supported, for example, on charcoal. The reaction may conveniently be carried out in a suitable solvent such as an alcohol (for example ethanol), an amide (for example dimethylformamide) an ether (for example tetrahydrofuran) and at a suitable temperature.

Compounds of formula (V) may be prepared, for example, from compounds of formula (VI)

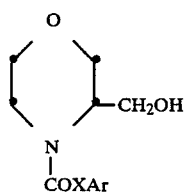

(VI)

by oxidation using conventional methods, for example using an oxidising agent such as chromium trioxide in a suitable solvent, for example pyridine.

Compounds of formula (VI) may themselves be prepared from a compound of formula (VII)

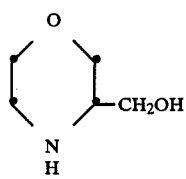

(VII)

by methods analogous to those described for general process (A) above. The compounds of formula (VII) may be prepared from compound (IV) by reduction using a suitable reducing agent, for example lithium aluminium hydride.

The general process described above may yield the product of the general formula (I) as an individual stereoisomer or as a mixture of stereoisomers. Diastereoisomers may be separated at any convenient point in the overall synthesis by conventional methods for example chromatography. Specific enantiomers may be obtained by resolution of a racemic mixture at any convenient point in the overall synthesis by the use of conventional methods, see for example "Stereochemistry of Carbon Compounds by E. L. Eliel" (McGraw Hill, 1962).

Where it is desired to isolate a compound of the invention as a salt, this may be formed by conventional methods, for example by treatment with an acid or base in a suitable solvent such as an ether (for example diethyl ether), a nitrile (for example acetonitrile), a ketone (for example acetone) a halogenated hydrocarbon (for example dichloromethane) or an ester (for example ethyl acetate). Salts may also be formed by conversion of one salt into another using conventional methods.

Thus the product of either of processes (A) to (B) above may be subjected to one or two further reactions comprising (1) converting a compound of formula (I) or a salt thereof into a physiologically acceptable salt thereof.
(2) resolution of a racemic mixture to give a specific enantiomer.

The invention is further illustrated by the following non-limiting examples.

All temperatures are in °C. Dried refers to drying with $Na_2SO_4$ unless otherwise indicated. S=singlet, m=multiplet.

EXAMPLE 1

4-[(3,4-Dichlorophenyl)acetyl]-3-(1-pyrrolidinylmethyl)morpholine maleate (1:1)

(i) Methyl 3-morpholinecarboxylate

Morpholine-3-carboxylic acid hydrochloride (1.04 g) was dissolved in methanol (20 ml) and the solution cooled to −20° C. Thionyl chloride (1 ml) was added dropwise to the stirred reaction mixture such that the temperature did not rise above −10°. After the addition was complete the reaction mixture was stirred at room temperature for 16 h. The solvent was removed in vacuo and the resultant pale grey residue was partitioned between 2N $Na_2CO_3$ and dichloromethane. The organic phase was separated, dried, and the solvent was removed in vacuo to give the title compound as an oil (220 mg).

Nmr δ ($CDCl_3$) 2.24 (1H, s), 2.8–3.1 (2H, m), 3.55–4.05 (5H, m), 3.76 (3H, s).

(ii) 1-[(3-Morpholinyl)carbonyl]pyrrolidine

The product of Stage (i) (204 mg) and distilled pyrrolidine (1 ml) were heated at 110° in a sealed vessel for 3 h. The pyrrolidine was removed in vacuo and the residue purified by column chromatography on silica gel (Art 7734) eluting with dichloromethane-methanol (10:1) to give the title compound as a crystalline solid (195 mg) m.p. 114°–117°

(iii) 3-(1-Pyrrolidinylmethyl)morpholine

To a suspension of lithium aluminium hydride (380 mg) in dry tetrahydrofuran (THF) (15 ml) was added a solution of the product of stage (ii) (400 mg), in dry THF (10 ml), under nitrogen. The reaction mixture was stirred under nitrogen and heated under reflux for 7 h. The mixture was allowed to cool to room temperature and then quenched by sequential addition of wet THF, water (0.4 ml), and 2N sodium hydroxide (1.2 ml) and the resultant mixture was filtered. The filtrate layers were separated and the aqueous layer was extracted with dichloromethane. The combined organic phases were dried, and the solvent was removed in vacuo to give the title compound as an oil (330 mg) which was used directly in the next stage.

(iv) 4-[(3,4-Dichlorophenyl)acetyl]-3-(1-pyrrolidinylmethyl)morpholine maleate (1:1)

To a solution of 3,4-dichlorophenylacetic acid (410 mg) in acetonitrile (10 ml) was added a solution of 1,1'-carbonyldiimidazole (340 mg) in warm acetonitrile (10 ml). After 10 min a solution of the product of stage (iii) (330 mg) was added and the mixture was stirred at room temperature for 3.5 h. The solvent was removed in vacuo and the residue was partitioned between dichloromethane (40 ml) and 2N sodium carbonate (30 ml). The organic phase was separated and washed with water (20 ml). The dried organic layer was evaporated and the oily residue (0.77 g) was purified by column chromatography on alumina (Type UGI), eluting with ethyl acetate, to give the free base of the title compound as a gum (462 mg) a portion of which (452 mg) was treated with maleic acid (147 mg) and crystallised from ethyl acetate to give the title compound (365 mg), m.p. 129°–131°.

Analysis Found C, 53.41; H, 5.49; N, 5.78. $C_{17}H_{22}Cl_2N_2O_2 \cdot C_4H_4O_4$ requires C, 53.29; H, 5.54; N, 5.92%

The following Examples illustrate pharmaceutical formulations containing 4-[(3,4-Dichlorophenyl)acetyl]-3-(1-pyrrolidinylmethyl)morpholine maleate as active ingredient. Other compounds of formula (I) may be formulated in a similar manner.

TABLETS FOR ORAL ADMINISTRATION
DIRECT COMPRESSION

|  | mg/tablet |
|---|---|
| Active ingredient | 20 |
| Calcium Hydrogen Phosphate B.P.* | 75.5 |
| Croscarmellose sodium USP | 4 |
| Magnesium Stearate, B.P. | 0.5 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

INJECTION FOR INTRAVENOUS ADMINISTRATION

|  | mg/ml |
|---|---|
| Active ingredient | 5 |
| Sodium Chloride BP | as required |
| Water for Injection BP 0.5 to 2 ml |  |

INTRAVENOUS INFUSION

| Dextrose 5% aqueous solution BP | 10–100 ml |
|---|---|
| Active ingredient | 700 mg |
| Sodium Chloride BP | as required |

For infusion at a rate of 700 mg per hour.

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass.

The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound of formula (I)

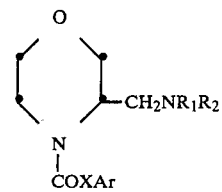

wherein
$R_1$ and $R_2$ are the same or different and are $C_{1-6}$ alkyl or $C_{3-6}$ alkenyl; or $-NR_1R_2$ forms a 5-membered (optionally containing an oxygen atom adjacent to the nitrogen) or a 6-membered ring, which ring optionally contains one unit of unsaturation and which is unsubstituted or substituted by hydroxy, oxo, optionally substituted methylidene, $-COR_3$ (where $R_6$ represents $C_{1-6}$ alkyl, $OR_4$ or $-NHR_4$, and $R_4$ represents hydrogen, $C_{1-6}$ alkyl, aryl, ar($C_{1-6}$)alkyl) or $=NOR_5$ (where $R_5$ represents $C_{1-6}$ alkyl);

X represents a direct bond, $-CH_2-$ or $-CH_2O-$;

Ar represents a substituted phenyl moiety;

and physiologically acceptable salts thereof.

2. A compound according to claim 1 wherein $-NR_1R_2$ represents a tetrahydropyridine or pyrrolidine ring.

3. A compound according to claim 2 wherein $-NR_1R_2$ represents a pyrrolidine ring.

4. A compound according to claim 1 wherein X represents $-CH_2-$ and Ar represents halosubstituted phenyl.

5. 4-[(3,4-Dichlorophenyl)acetyl]-3-(1-pyrrolidinylmethyl)morpholine and its physiologically acceptable salts.

6. A pharmaceutical composition which comprises an effective amount of a compound of formula (I) as defined in claim 1 or a physiologically acceptable salt thereof together with a pharmaceutically acceptable carrier thereof.

7. A method of treating a human suffering from pain or cerebral ischaemia which comprises administering an effective amount of a compound of formula (I) as defined in claim 1 or a physiologically acceptable salt thereof.

* * * * *